(12) United States Patent
Bauer et al.

(10) Patent No.: US 11,553,875 B2
(45) Date of Patent: Jan. 17, 2023

(54) SYSTEM AND DEVICE FOR IMPROVING SLEEP QUALITY

(71) Applicant: George Kirkman, Palos Verdes Estates, CA (US)

(72) Inventors: Hannah Bauer, Rolling Hills Estates, CA (US); Joseph Bravo, Torrance, CA (US); Albert Chen, Torrance, CA (US); Alexander Hool, Palos Verdes, CA (US); Michael Huang, Palos Verdes Estates, CA (US); Aaron Isara, Torrance, CA (US); Aaron Jung, Palos Verdes Estates, CA (US); Josef Kirkman, Palos Verdes Estates, CA (US); Joyce Lee, Carson, CA (US); Lucas Loman, Hermosa Beach, CA (US); Sharon Maguey, Lakewood, CA (US); Kathryn Saxton, Torrance, CA (US); Lian Zhu, Torrance, CA (US); George Kirkman, Palos Verdes Estates, CA (US)

(73) Assignee: Rolling Robots, Inc., Los Angeles, CA (US)

( * ) Notice: Subject to any disclaimer, the term of this patent is extended or adjusted under 35 U.S.C. 154(b) by 333 days.

(21) Appl. No.: 16/886,788

(22) Filed: May 29, 2020

(65) Prior Publication Data

US 2021/0369190 A1    Dec. 2, 2021

(51) Int. Cl.
| | | |
|---|---|---|
| *A61B 5/00* | (2006.01) | |
| *A61B 5/16* | (2006.01) | |
| *A61B 5/01* | (2006.01) | |
| *A61B 5/25* | (2021.01) | |

(52) U.S. Cl.
CPC .......... *A61B 5/4815* (2013.01); *A61B 5/0048* (2013.01); *A61B 5/01* (2013.01); *A61B 5/163* (2017.08); *A61B 5/25* (2021.01); *A61B 5/6814* (2013.01)

(58) Field of Classification Search
CPC .......... A61B 5/25; A61B 5/01; A61B 5/4815; A61B 5/163; A61B 5/0048; A61B 5/6814
See application file for complete search history.

(56) References Cited

U.S. PATENT DOCUMENTS

| | | | |
|---|---|---|---|
| 2012/0063487 A1* | 3/2012 | Albrecht | A61B 5/6817 374/128 |
| 2014/0277308 A1* | 9/2014 | Cronise | A61F 7/00 607/112 |
| 2020/0139112 A1* | 5/2020 | Aharonovitch | A61B 5/4812 |

* cited by examiner

*Primary Examiner* — Benyam Haile (57) ABSTRACT

A device and system for promoting more recuperative sleep by regulating a user's body temperature. This may be done by using a series of devices that measure information about the user both while they are awake and while they are asleep, communicate that information to a processing unit, and create an ideal body temperature range profile based on that information. A temperature stimulus device may ensure that the core body temperature of the user stays substantially within the ideal body temperature range. By keeping the core body temperature of the user within the calculated range, the device and system will ensure deeper, and therefore more recuperative, sleep.

1 Claim, 10 Drawing Sheets

SYSTEM AND DEVICE FOR IMPROVING SLEEP QUALITY

CROSS REFERENCE TO RELATED APPLICATION

This application claims the benefit of U.S. Provisional Application No. 62/855,207 filed on May 31, 2019, the contents of which are incorporated herein by this reference as though set forth in their entirety.

FIELD OF USE

The present disclosure relates generally to a method for improving sleep quality. More specifically, the present disclosure relates to a process of measuring brain waves, eye movement, and body temperature combined with measurements of alertness during waking hours to determine the quality of a person's sleep and using that information to provide stimuli that regulate body temperature in a manner that improves sleep quality.

BACKGROUND OF THE INVENTION

The amount of sleep a person gets is highly impactful on their overall physical and mental health. A study of 30,000 Virginian students found that of teens who often slept less than six hours a night, 30% suffered from depression, and roughly 10% attempted suicide. While the duration of sleep directly impacts a person's health, the quality of sleep is also important. Because deep sleep is the most efficient portion of the sleep cycle for recovery, when a larger percentage of a night's sleep is deep sleep—also known as slow-wave sleep—there is a greater positive impact on a person's recovery. The relationship between core body temperature and the amount of deep sleep is well known. If a person's body temperature can be properly regulated, it is possible to induce better, more effective sleep. While some devices may attempt this, these devices generally measure only the user's sleep data; and do not use data gathered while the user is awake to factor in the impact of the user's sleep.

There is, thus, a need in the art for a method of regulating a person's body temperature that uses natural sleep patterns as well as waking data to regulate body temperature in a manner that encourages more efficient sleep.

SUMMARY OF THE INVENTION

To minimize the limitations in the cited references, and to minimize other limitations that will become apparent upon reading and understanding the present specification, the present specification discloses a device and method for regulating a person's body temperature to promote better sleep.

In one embodiment, the device of the present disclosure may be a wearable headband and earpiece which utilizes electroencephalography (EEG) to measure a user's brain waves, eye movement, core body temperature, and pulse during sleep. The device may then transfer these measurements to an electronic device application that processes the information. The electronic device application may analyze the quality of the user's sleep with respect to body temperature and create a profile of the user's ideal body temperature during sleep. The application may then use a localized temperature stimulus, preferably found within a wearable device, to alter the body temperature of the user such that the body temperature of that user may be preferably maintained within the calculated ideal body temperature range.

In another embodiment, the device of the present disclosure may also have an electronic device application comprising several games. The games may be used to measure the user's reaction time and correlate it to the quality of sleep or core body temperature during sleep. The electronic device application may collect other data throughout the user's waking hours either passively or with the user's input. The electronic device application may also comprise an artificial intelligence system. The artificial intelligence system may measure the relationship between the factors the device measures both while the user is asleep and awake to calculate a temperature profile that best promotes efficient sleep. The localized temperature stimulus, electronic device application, and artificial intelligence system may communicate with each other through WiFi and/or Bluetooth. Using the correlation between the user's reaction time and the factors measured by the device, the electronic device application may adjust the user's core body temperature through the localized temperature stimulus.

Other features and advantages will become apparent to those skilled in the art from the following detailed description and its accompanying drawings.

DETAILED DESCRIPTION OF THE INVENTION

In the following detailed description of various embodiments, numerous specific details are set forth in order to provide a thorough understanding of various aspects of the embodiments. However, the embodiments may be practiced without some or all of these specific details. In other instances, well-known procedures and/or components have not been described in detail so as not to unnecessarily obscure aspects of the embodiments.

While some embodiments are disclosed here, other embodiments will become obvious to those skilled in the art as a result of the following detailed description. These embodiments are capable of modifications of various obvious aspects, all without departing from the spirit and scope of protection. The Figures and their detailed descriptions are to be regarded as illustrative in nature and not restrictive.

Also, the reference or non-reference to a particular embodiment shall not be interpreted to limit the scope of protection.

In the following description, certain terminology is used to describe certain features of one or more embodiments. For purposes of the specification, unless otherwise specified, the term "substantially" refers to the complete or nearly complete extent or degree of an action, characteristic, property, state, structure, item, group of items, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, group of items, or result. In another example, substantially all of a group of items may include all of the items of that group, or at least all of the items of that group that are generally within the normal parameters for the items. To the extent that the group of items might include members that far exceed the normal parameters, this abnormal item might not be expected to be part of substantially all the group of items.

One embodiment of the present disclosure may be a system and device that improves sleep quality. The device may comprise three parts: a system of components that gather data from the user, a component that processes that data, and a component that alters the user's body temperature based on that processed data.

Figure 1:
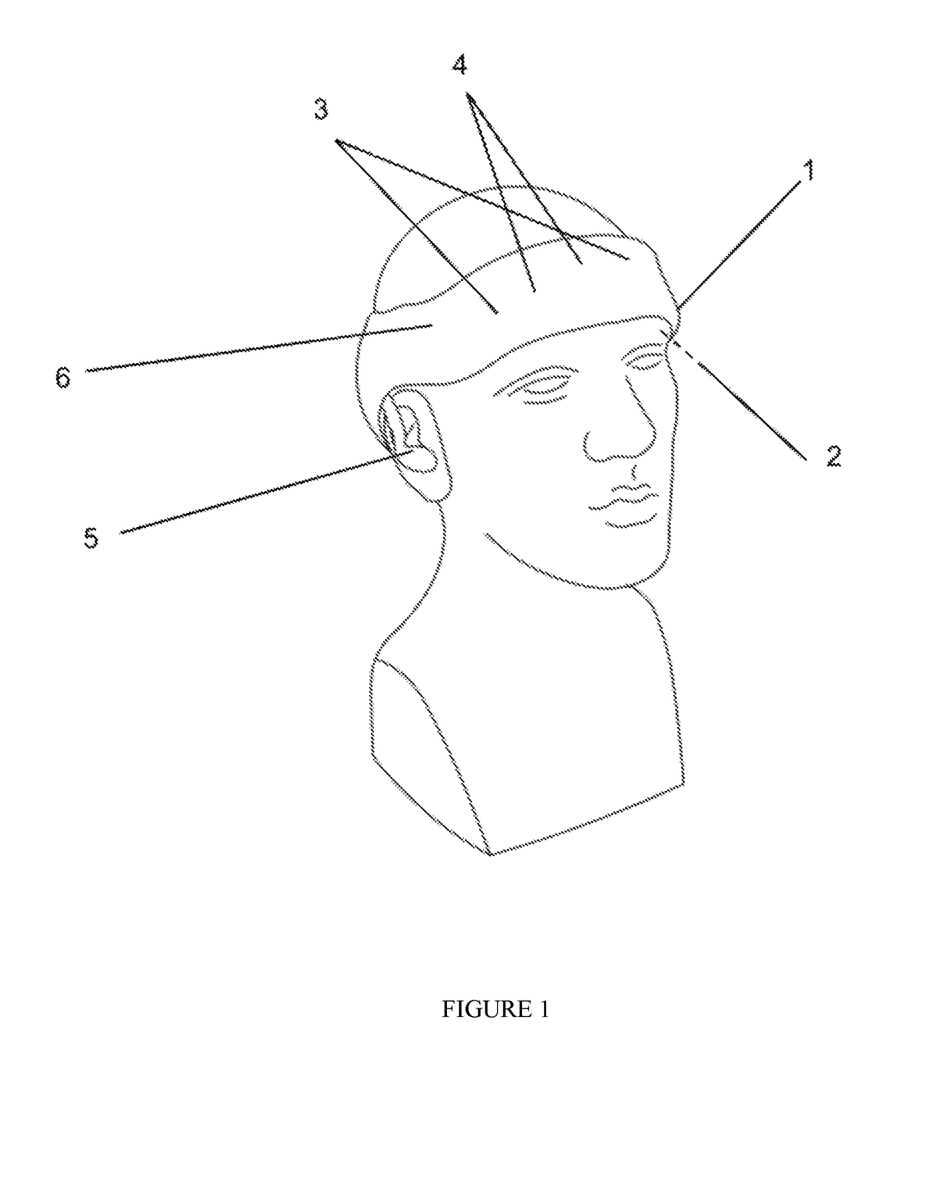
FIG. 1 is a perspective view of the headband device incorporating a multiplicity of sensors to monitor sleep.
Figure 2:
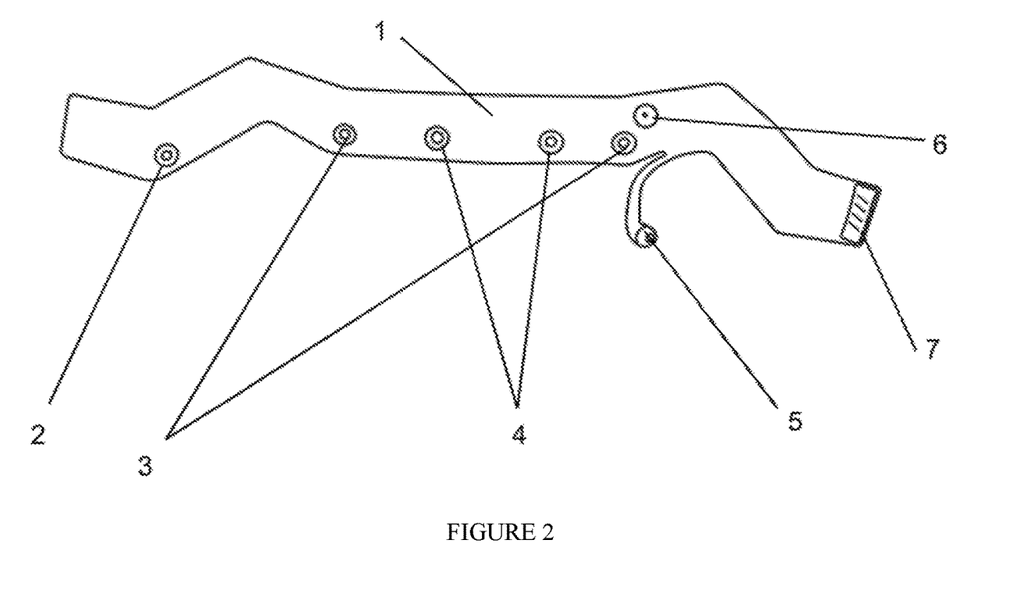
FIG. 2 is a view of the inner side of the headband device of FIG. 1.

The system of components that gather data may measure several variables from the user such as core body temperature, brain waves, heart rate, eye movement, body movement, breathing rate, and/or other information associated with sleep quality. Referring to FIGS. 1-2, this system of components may take the form of a headband 1. The headband 1 may be the main element of physical data input from the user. A pair of electroencephalogram (EEG) electrodes 4 located at the front of the headband are positioned on the user's forehead to detect and measure brain waves. Located laterally to the EEG electrodes is a pair of electrooculogram (EOG) electrodes 3, which detect and measure eye muscle movement. The data outputted by the electrodes are compared to that of a reference ground electrode 2 positioned behind the user's ear to account for external variables that may influence data. An earpiece 5 containing an infrared temperature sensor drops down from the headband to be positioned in the right or left ear. The sensor detects and measures the core body temperature of the user. A heart rate sensor 6 may be positioned on the user's temple to detect and measure the heart rate of the user. A Velcro strap 7 may be located on the headband to securely fit the headband around the user's head.

Figure 3:
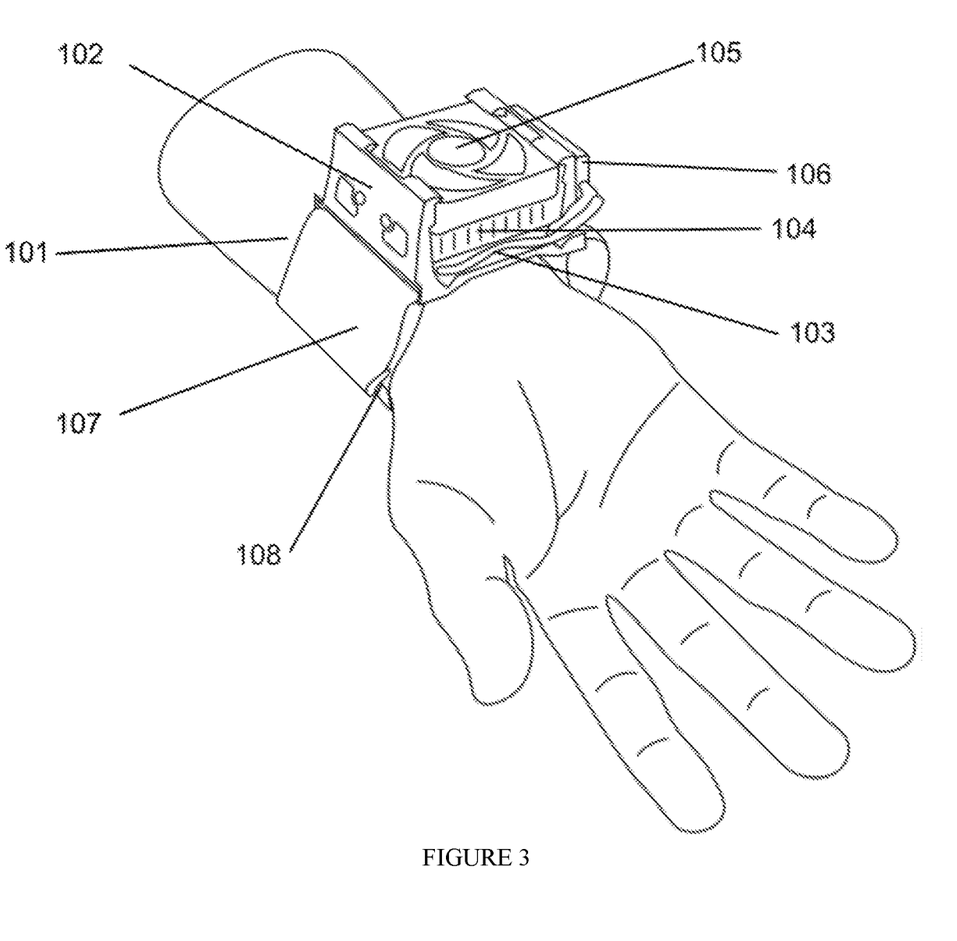
FIG. 3 is a perspective view of the wristband device for providing stimuli to the user.
Figure 4:
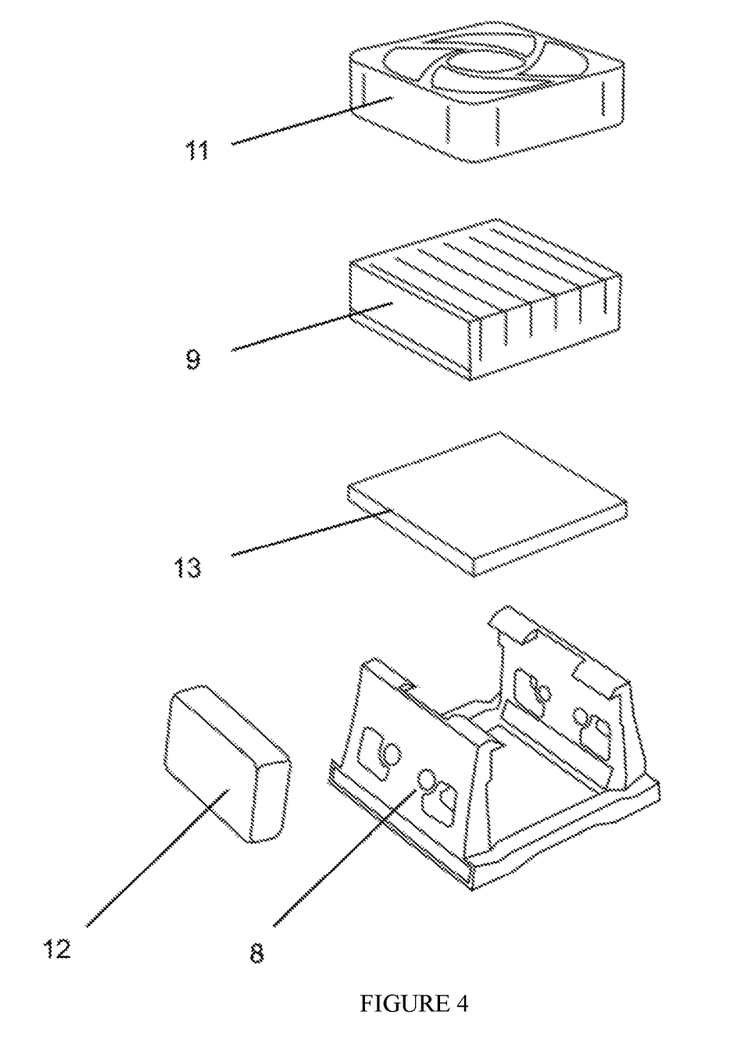
FIG. 4 is an exploded view of the wristband device of FIG. 3.

Referring now also to FIGS. 3-4 a device to provide stimuli to the user may be incorporated into a wrist device 101. Said wrist device 101 may be the main element of stimulus output for the system. The adjustable elastic wristband 107 and Velcro attachment 108 allow for a secure fit of the device around the user's wrist. The electric components of the device are substantially contained in the housing 102 that connects to the wristband 107. A Peltier cooler 103 device provides a variable temperature stimulus to the user through contact with the palm side of the wrist. A heat sink 104 and heat dissipation fan 105 work in tandem to neutralize the relative warmth or coldness on the side of the Peltier cooler that faces away from the user's wrist. A temperature controller 106 allows the system to communicate with the wrist device and control the Peltier cooler output.

In order to measure temperature, the system of components may comprise a temporal artery thermometer, a topical thermometer, an in-ear thermometer, or any combination thereof. When measuring body movement, eye movement, and brain waves the system may comprise gyroscopes, accelerometers, EEG electrodes, EMG electrodes, an electroencephalogram, or a method of electrooculography. CBT may also be measured through use of an infrared sensor. Measuring the brain waves and eye movement in a consumer device is unique, as it most clearly indicates the user's sleep stages by showing when the user is in slow-wave sleep.

Figure 5:
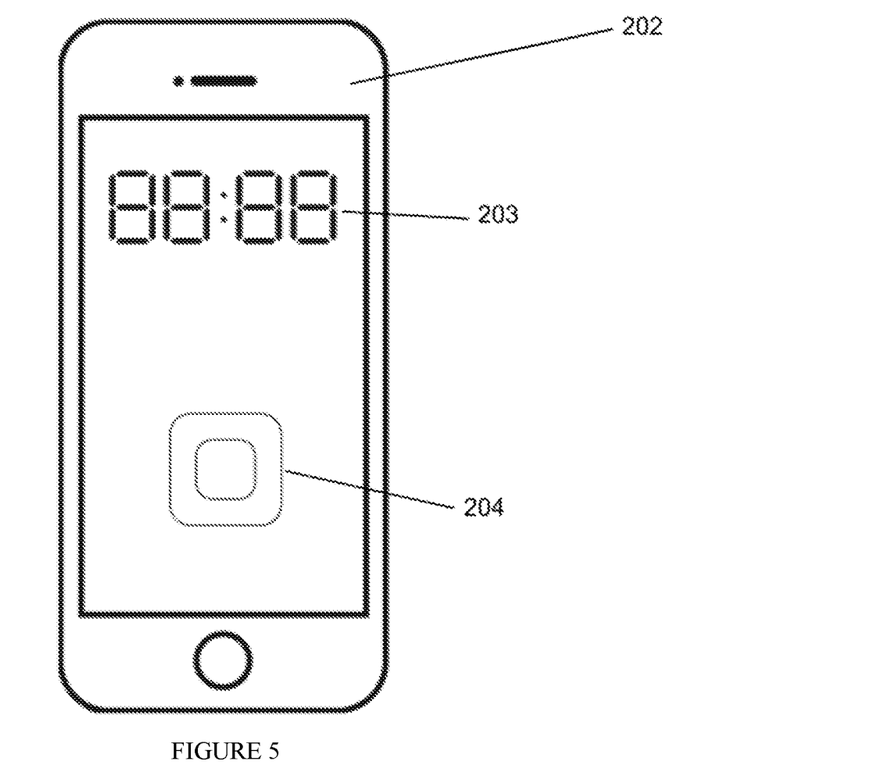
FIG. 5 is a screen view of an application to measure reaction time on an electronic device.
Figure 6:
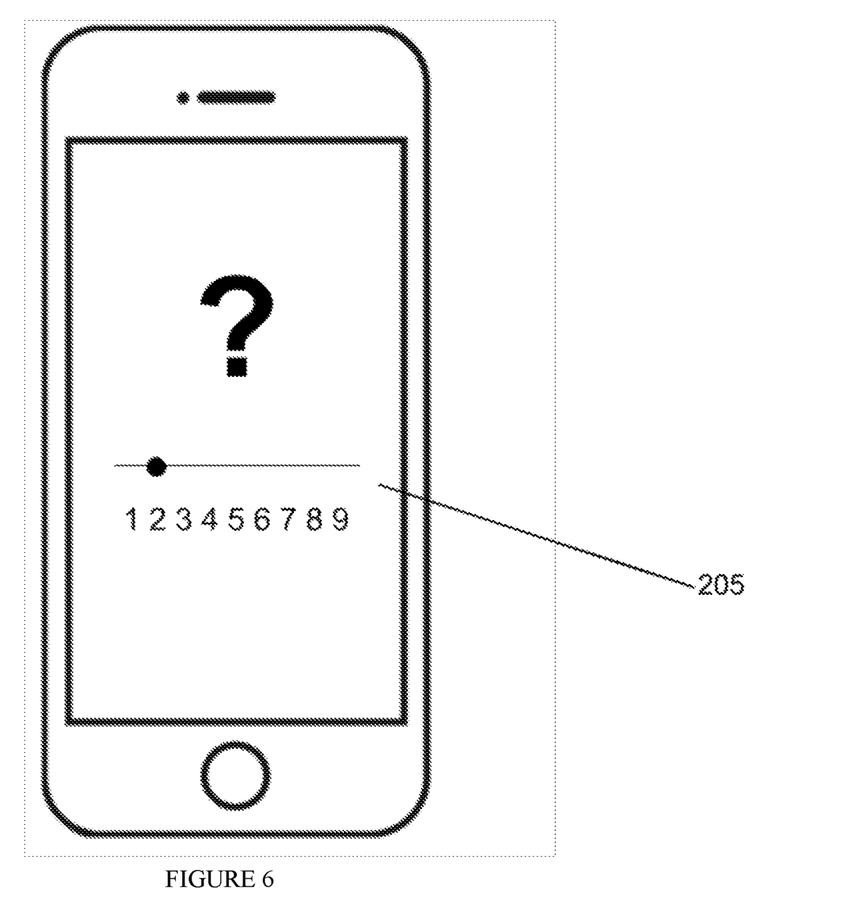
FIG. 6 is a screen view of an application to survey sleepiness on an electronic device.
Figure 7:
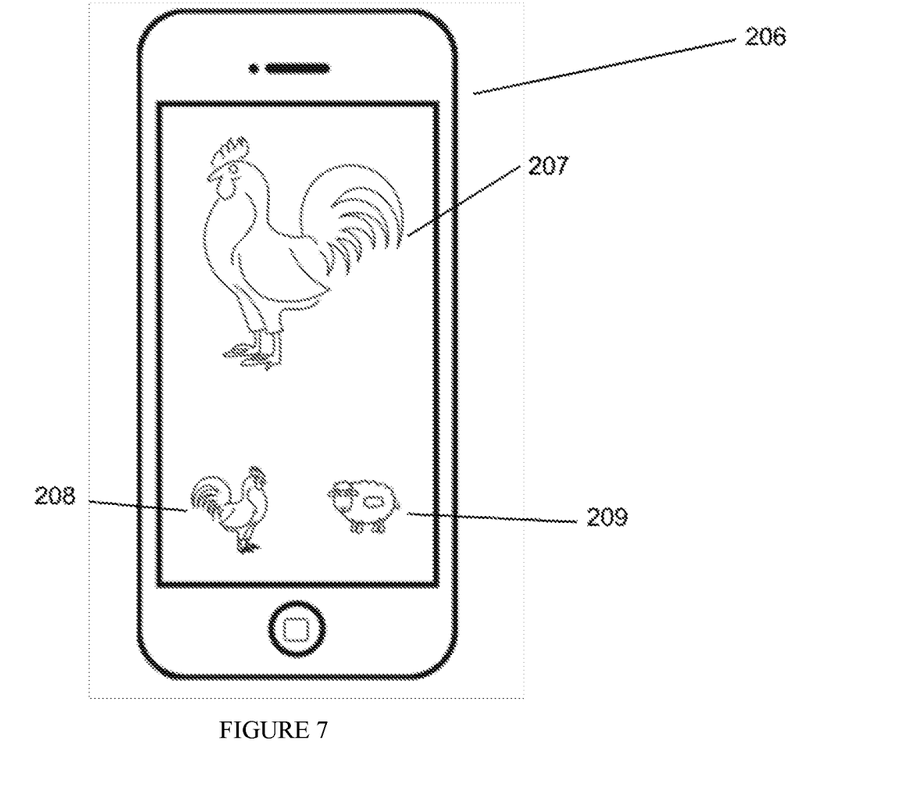
FIG. 7 is a screen view of an application to measure cognitive ability on an electronic device.

Referring now also to FIGS. 5-7 a mobile application 201 may be the main element of daily user input. A reaction time game 202 tests and measures the user's ability to react quickly to prompts given by the game, which the user can do by pressing the reaction time button 204. The reaction timer 203 shows the amount of time taken by the user to correctly respond to the game's prompts. A study of drivers has shown reaction time correlated to sleepiness. As well as an increased accident rate with lack of sleep. Hence reaction time is a measure of how well the user has been sleeping. A sleepiness scale survey 205 allows the user to input a relative value based on their level of drowsiness. In one embodiment the survey may use a method such as the Karolinska Sleepiness Scale that is a subjective measure of how likely the user is to doze during certain situations. It is a self reported test and as such is subject to variation from user to user. For any individual user at a specific time of day it may be a scale with high validity. Another evaluation of alertness is a cognitive recognition test 206. Said test combines reaction speed with ability to make decisions. In one embodiment an animal recognition game 206 tests the user's decision-making ability, which the user can interact with using the two animal option buttons 208, 209. All games and surveys may be combined to assess the user's quality of sleep from previous nights.

In one embodiment, the electronic device is a smartphone communicatively connected to the system and device which also measures information about the user while they are awake such as their circadian rhythm. In measuring performance while awake in conjunction with the user's location within their circadian rhythm, the device determines the impact of the quality of sleep on the user with respect to the user's daytime attentiveness and general performance. Although not stated herein, other information may be gathered through other measurement devices not explicitly named. The data gathered by this system of components may be transferred to an electronic device through WiFi, Bluetooth, cable, manually, or a combination thereof.

Figure 8:
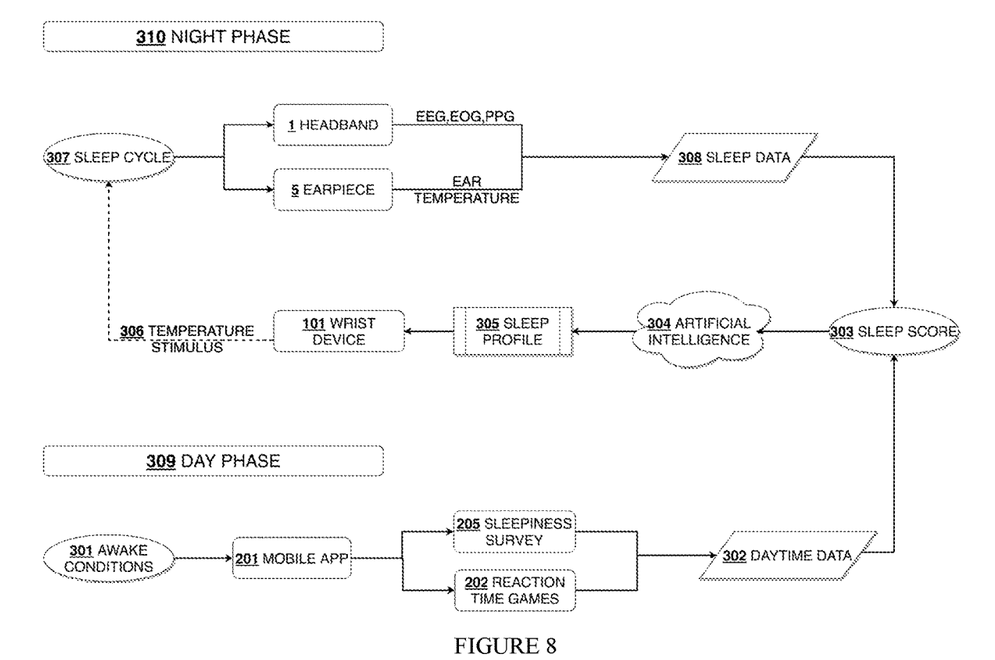
FIG. 8 is a flowchart showing the operation of the system and device.

Referring now also to FIG. 8 the flowchart illustrates the system's data inputs and corresponding outputs. The night phase 310 indicates the aspects of the system that occur while the user sleeps, while the day phase 309 indicates the aspects that occur while the user is awake. The awake conditions 301 indicate daytime characteristics of the user, such as reaction time and quality of sleep, which are measured by the mobile app 201 in the form of the sleepiness survey 205 and reaction time games 202 to generate the daytime data 302. In the night phase, the user's sleep cycle 307 indicates the nighttime characteristics of the user, which is primarily the sleep cycle. These characteristics are measured by the headband 1 and earpiece 5 to generate sleep data 308, which, along with the daytime data, is used to generate the user's sleep score 303. The system's artificial intelligence 304 analyzes the data to produce a personalized sleep profile 305 that determines a model for stimulus application. The wrist device 101 follows the model to apply a temperature stimulus 306 that actively influences the user's next night of sleep. In turn, the altered sleep cycle for the next night and the next day's daytime inputs lead to a new sleep profile and stimulus model.

The component that processes data may be an application on a user's electronic device which is preferably a smartphone. Said electronic device may be communicatively connected to the headband measurement device 1 and the wrist stimulus device 101 as well as a cloud database 302, 308. An artificial intelligence system 302 may be incorporated into the application to interpret the data independent of the user's input. After interpreting the data, the artificial intelligence system within the application may create a set of ideal temperature ranges where the user is more likely to enter a deeper, and therefore more efficient for recovery, level of sleep. Core body temperature decreases throughout the sleep process; the artificial intelligence system may continuously monitor the core body temperature of the sleeping user and regulate the temperature through the use of a temperature stimulus. Ideally, the temperature stimulus alters the user's skin temperature, manipulating the user's core body temperature to encourage more efficient slow-wave sleep. Similarly, the artificial intelligence system will incorporate measurements taken during daytime when analyzing ideal sleep temperature to improve not only the impact on sleep quality, but daytime performance. In processing these nighttime and daytime factors, the artificial intelligence system creates a temperature profile which the user may modify if desired. Even without the user's direct input, the artificial intelligence system will fine-tune the temperature profiles as it gathers more data, continuing to optimize efficiency.

The Logic is based in the Sleep Profile. Each sleep profile is personalized to each user through Artificial Intelligence optimization. The Effectiveness of the sleep profile is judged based on the user's sleep score corresponding to that given sleep profile. An example sleep profile may consist of logic as follows: if the user is coming out of a deep sleep stage, apply a warm temperature stimulus to guide the user back to the deep sleep stage. The daytime data is interpreted through Artificial Intelligence which may consist of logic as follows: if Sleep Profile A resulted in a lower Sleep Score than Sleep Profile B, remove Sleep Profile A from the options and pursue Sleep Profile B.

The temperature stimulus may create heat such that it regulates the user's body temperature. This stimulus may take the form of a wearable device, such as a wristband, watch, necklace, or other easily removable articles. The stimulus may also be larger, taking the form of a shirt, or even a blanket. Ideally, the stimulus creates enough heat such that it may change, and therefore regulate, the core body temperature of the user.

Figure 9:
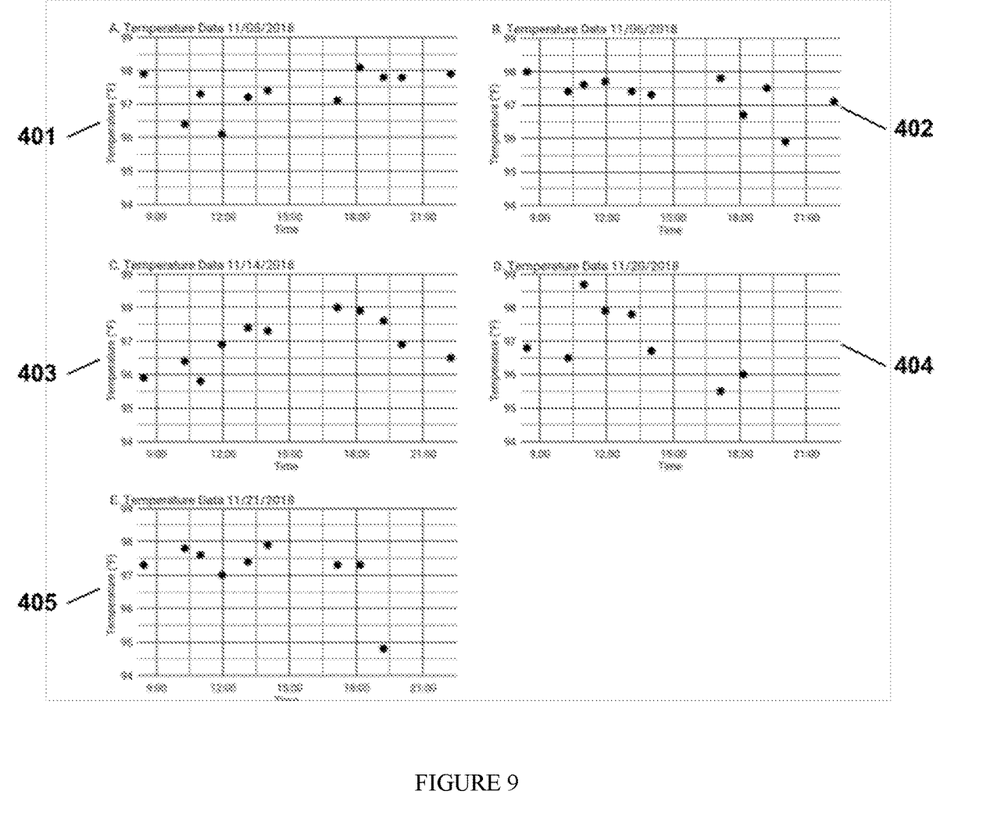
FIG. 9 is a collection of core body temperature measurements for a specific user.

Referring now also to FIG. 9 showing a collection of temperature measurements 401-405 for a single user. Here temperature was measured using an infrared sensor ear thermometer. Change of core body temperature is observed and correlated to a circadian rhythm. Temperature was measured at different times of day and over several days. This data combined with the daytime alertness data can be used in a two factor model to predict sleepiness.

Figure 10:
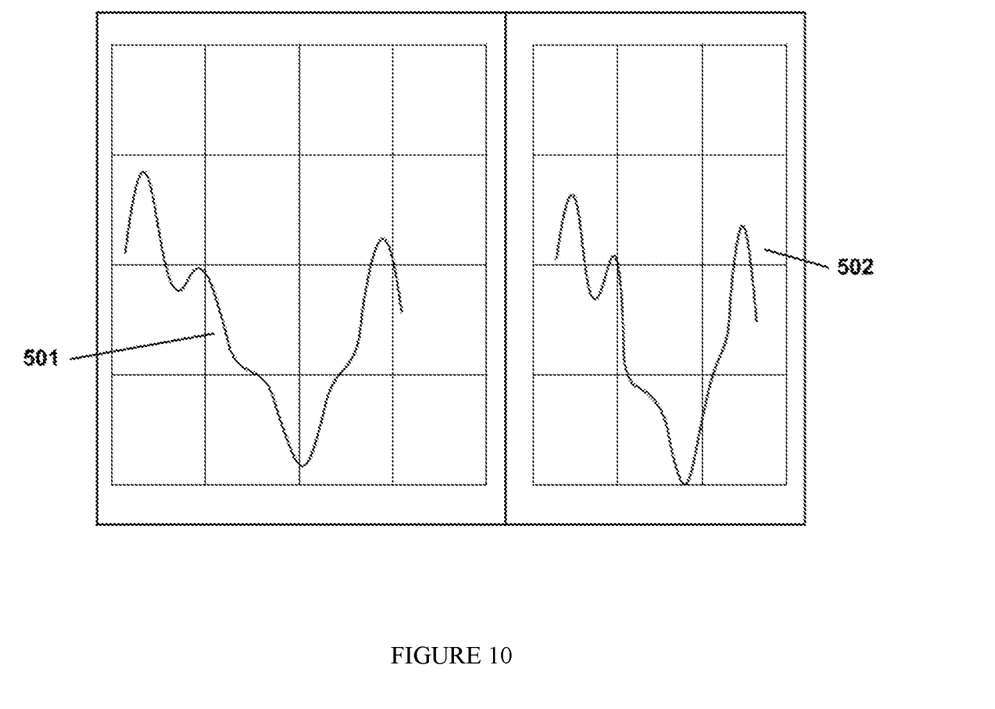
FIG. 10 is a measurement of a simulated brain wave using the system and device.

Referring now also to FIG. 10 showing a measurement of a simulated 501 brain wave. The voltage level 502 is arbitrary but consistent with what a typical user would produce. Brain waves are the true indicator of sleep stage. Being able to measure 502 the brain wave enables determination of the sleep stage that may be compared with daytime data to judge the quality of different sleep stages.

The drawings show illustrative embodiments, but do not depict all embodiments. Other embodiments may be used in addition to or instead of the illustrative embodiments. Details that may be apparent or unnecessary may be omitted for the purpose of saving space or for more effective illustrations. Some embodiments may be practiced with additional components or steps and/or without some or all components or steps provided in the illustrations. When different drawings contain the same numeral, that numeral refers to the same or similar components or steps.

Unless otherwise stated, all measurements, values, ratings, positions, magnitudes, sizes, locations, and other specifications that are set forth in this specification, including in the claims that follow, are approximate, not exact. They are intended to have a reasonable range that is consistent with the functions to which they relate and with what is customary in the art to which they pertain.

The foregoing description of the preferred embodiment has referred to night time data and daytime data interchangeably with sleep data and awake data. It is recognized that different users may have alternate sleep hours. Considering this no particular time of day is implied by these terms.

The foregoing description of the preferred embodiment has been presented for the purposes of illustration and description. While multiple embodiments are disclosed, still other embodiments will become apparent to those skilled in the art from the above-detailed description. These embodiments are capable of modifications in various obvious aspects, all without departing from the spirit and scope of protection. Accordingly, the detailed description is to be regarded as illustrative in nature and not restrictive. Also, although not explicitly recited, one or more embodiments may be practiced in combination or conjunction with one another. Furthermore, the reference or non-reference to a particular embodiment shall not be interpreted to limit the scope of protection. It is intended that the scope of protection not be limited by this detailed description, but by the claims and the equivalents to the claims that are appended hereto.

Except as stated immediately above, nothing that has been stated or illustrated is intended or should be interpreted to cause a dedication of any component, step, feature, object, benefit, advantage, or equivalent, to the public, regardless of whether it is or is not recited in the claims.

What is claimed is:

1. A system for improving sleep quality, comprising:
   a headband;
   a localized temperature stimulus; and
   an electronic device;
   wherein said headband is configured to be worn by a user;
   wherein said headband comprises two electroencephalogram electrodes, two electrooculogram electrodes; a reference ground electrode; an infrared temperature sensor; and a heart rate sensor;
   wherein said two electroencephalogram electrodes are configured to measure a plurality of brainwaves of said user;
   wherein said two electrooculogram electrodes are configured to measure a plurality of eye muscle movements of said user;

wherein when said headband is worn by said user, said two electroencephalogram electrodes are configured to rest against a forehead of said user;

wherein said two electroencephalogram electrodes are oriented on said headband such that said two electroencephalogram electrodes are between said two electrooculogram electrodes;

wherein said reference ground electrode is oriented on said headband such that when said headband is worn by said user, said reference ground electrode is located above and behind an ear of said user;

wherein said infrared temperature sensor is configured to hang downward from said headband, such that when said headband is worn by said user, said infrared temperature sensor is able to measure a core body temperature of said user through said ear of said user;

wherein said heart rate sensor is oriented on said headband such that when said headband is worn by said user, said heart rate sensor rests against said user's temple;

wherein said localized temperature stimulus is a wrist device;

wherein said wrist device comprises a strap, a housing, a Peltier cooler, a heat sink, and heat dissipation fan;

wherein said headband and said wrist device are in electronic communication with said electronic device;

wherein said electronic device comprises a software application configured to collect data provided by said headband;

wherein said electronic device is a mobile phone;

wherein said software application comprises one or more games configured to measure a reaction time of said user, wherein said reaction time is a metric for determining said an overall sleep quality of said user;

wherein said software application is configured to collect user data from said headband;

wherein said user data is sorted by awake condition data and sleep cycle data;

wherein said awake condition data comprises one or more daytime characteristics of said user;

wherein said one or more daytime characteristics comprise at least a reaction time and a quality of sleep;

wherein said reaction time is determined based on said user playing one of said one or more games on said electronic application and recording a game data;

wherein said quality of sleep is determined based on said user responding to a sleepiness survey on said software application;

wherein said sleep cycle data comprises EEG data collected by said two electroencephalogram electrodes, EOG data collected by said two electrooculogram electrodes, PPG data collected by said reference ground electrode, ear temperature data collected by said infrared temperature sensor, and an activity by said wrist device;

wherein said awake condition data and said sleep cycle data are processed by an artificial intelligence to generate a sleep profile of said user;

wherein said electronic device is configured to use said sleep profile to determine when and how to activate said wrist device, such that said wrist device is configured to alter a core body temperature of said user to cause said user to enter a more restful sleep;

wherein said sleep profile of said user comprises measurements collected by said headband spanning a plurality of days and nights, such that said system for improving sleep quality is configured to track and record said sleep cycle data and correlate said sleep cycle data with said awake condition data to determine how said activity by said wrist device affects said awake condition data in order to determine what future activity of said wrist device should be to allow said user to enter into said more restful sleep.

* * * * *